United States Patent [19]

Steber

[11] Patent Number: 5,213,810

[45] Date of Patent: May 25, 1993

[54] STABLE COMPOSITIONS FOR PARENTERAL ADMINISTRATION AND METHOD OF MAKING SAME

[75] Inventor: William Steber, Ledgewood, N.J.

[73] Assignee: American Cyanamid Company, Stamford, Conn.

[21] Appl. No.: 502,382

[22] Filed: Mar. 30, 1990

[51] Int. Cl.⁵ .................................................. A61K 9/16
[52] U.S. Cl. ................................... 424/490; 424/493; 424/484; 424/502; 424/438
[58] Field of Search .............. 424/502, 484, 493, 438, 424/490; 514/772, 538; 470/470; 435/69.4

[56] References Cited

U.S. PATENT DOCUMENTS

| 3,147,187 | 9/1964 | Playfair | 424/502 |
| 4,452,775 | 6/1984 | Kent | 514/772 |
| 4,483,847 | 11/1984 | Augart | 424/470 |
| 4,568,536 | 2/1986 | Kronenthal | 424/484 |
| 4,568,559 | 2/1986 | Nuwayser | 424/493 |
| 4,666,839 | 5/1987 | Souza | 435/69.4 |
| 4,696,914 | 9/1987 | Rüsse | 514/538 |
| 4,837,381 | 6/1989 | Steber et al. | 424/438 |

Primary Examiner—Thurman K. Page
Assistant Examiner—William E. Benston
Attorney, Agent, or Firm—John W. Hogan, Jr.

[57] ABSTRACT

The invention relates to certain stable microsphere compositions suitable for parenteral administration containing a fat or wax or mixture thereof; a biologically active protein, peptide or polypeptide; and an oil, semi-soft fat, fatty acid derivative or mixture thereof. The invention also relates to a method of making the microsphere compositions.

20 Claims, No Drawings

STABLE COMPOSITIONS FOR PARENTERAL ADMINISTRATION AND METHOD OF MAKING SAME

BACKGROUND OF THE INVENTION

U.S. Pat. No. 4,837,381 discloses a microsphere composition of fat or wax or mixture thereof and a biologically active protein, peptide or polypeptide suitable for parenteral administration. The patent discloses the utility of the compositions for slow release of a protein, peptide or polypeptide in a parenteral administration, and discloses methods for increasing and maintaining increased levels of growth hormone in the blood of treated animals for extended periods of time and thereby increasing weight gains in animals and increasing milk production of lactating animals by the administration of compositions of the invention.

There are special problems in the development of sustained release pharmaceutical compositions of biologically active macromolecules due to the size and complexity of the macromolecules, particularly proteins, which are susceptible to chemical and structural alteration upon mixing with pharmaceutical excipients, upon processing and upon storage. These problems are understood by those skilled in the art of pharmaceutical formulation and can be categorized as problems of chemical stability. Inadequate chemical stability of pharmaceutical compositions resulting from irreversible alteration of the structure of the macromolecules and/or interactions with the excipients can result in compositions that are either inactive or do not provide the expected level of biological response.

Another category of problems for pharmaceutical formulations is physical stability. One obvious example is attrition of tablets or implants during processing, packaging, or storage. Another example is a physical separation of a cream, paste or gel into component parts which can lead to a heterogeneous distribution of active ingredient as well as alteration of the consistency. The consequence of such physical deterioration of the formulation can be loss of the desired ease of use characteristics and an unpredictable dosing to the patient. Less obvious physical changes in a pharmaceutical formulation include various alterations to the crystalline or microscopic structure of the excipients. These types of changes can lead to marked alterations in the release of active agents. It should be clear that changes in the physical stability of pharmaceutical dosage forms whether they be for oral or parenteral administration would be most problematic for sustained release preparations. It is the sine qua non of commercially viable sustained release pharmaceutical dosage forms that they have maintained release characteristics across production lots and after relatively long periods of time in storage. Physical stability of the pharmaceutical dosage form is intended to describe both constancy of the handling characteristics such as hardness, flowability, or viscosity, and constancy of pharmacological performance.

It is an object of this invention to provide stable compositions for parenteral administration. It is another object of this invention to provide a novel method of preparing these stable compositions. It is still another object to provide a microsphere composition which can be packaged as a ready to use formulation with good storagability. These and other objects will become apparent in the description of the invention.

SUMMARY OF THE INVENTION

The present invention relates to unexpectedly stable microsphere compositions for parenteral administration. The compositions comprise on a weight basis about 30% to 95% of a fat or wax or mixture thereof about 2% to 70% of a biologically active protein, peptide or polypeptide and about 1% to 30% of an oil, semi-soft fat, fatty acid derivative or mixtures thereof.

The present invention also relates to a method of preparing the highly stable compositions at ambient temperatures. Surprisingly, it has been found that the addition of a small amount of oil, semi-soft fat and/or fatty acid derivative to the mixture of fats and/or waxes and the biologically active protein, peptide, or polypeptide before prilling allows accelerated transformation from the alpha crystalline structure to the beta form. Because the beta form is much more stable, the compositions of the invention show increased stability. This invention is especially surprising considering certain oils have been used as a vehicle for prior art compositions after prilling, but did not result in the accelerated crystal transformation.

DESCRIPTION OF THE PREFERRED EMBODIMENTS

The compositions are suitable for parenteral administration to animals. The biologically active proteins, peptides or polypeptides include growth hormones, somatomedins, growth factors, and other biologically active fragments or derivatives thereof.

The invention provides a microsphere composition which can be packaged as a ready to use formulation with good storagability because of its increased stability.

Waxes and fats which are suitable for use in the compositions of this invention in general have melting points higher than 40° C. The wax of the invention may be defined as set forth in Hawley's *The Condensed Chemical Dictionary*, Eleventh Edition, as a low-melting organic mixture or compound of high molecular weight, solid at room temperature and generally similar in composition to fats and oils except that it contains no glycerides. Some are hydrocarbons; others are esters of fatty acids and alcohols. These compounds include saturated or unsaturated long chain $C_{10}$–$C_{24}$ fatty acids, alcohols, esters, salts, ethers or mixtures thereof. They are classed among the lipids. Waxes are thermoplastic, but since they are not high polymers, they are not considered in the family of plastics. Common properties are water repellency; smooth texture; nontoxicity; freedom from objectionable odor and color. They are combustible and have good dielectric properties. They are soluble in most organic solvents and are insoluble in water. The major types are as follows:

I. Natural

1. Animal (beeswax, lanolin, shellac wax, Chinese insect wax)
2. Vegetable (carnauba, candelilla, bayberry, sugar cane)
3. Mineral
   (a) Fossil or earth waxes (ozocerite, ceresin, montan)
   (b) petroleum waxes (paraffin, microcrystalline) (slack or scale wax)

II. Synthetic

1. Ethylenic polymers and polyol ether-esters ("Carbowax," sorbitol)
2. Chlorinated naphthalenes ("Halowax")
3. Hydrocarbon type via Ficher-Tropsch synthesis The fat of the invention may be defined as set forth in Hawley's *The Condensed Chemical Dictionary*, Eleventh Edition, as a glyceryl ester of higher fatty acids such as stearic and palmitic. Such esters and their mixtures are solids at room temperatures and exhibit crystalline structure. Lard and tallow are examples. There is no chemical difference between a fat and an oil, the only distinction being that fats are solid at room temperature and oils are liquid. The term "fat" usually refers to triglycerides specifically, whereas "lipid" is all-inclusive.

The fat is preferably composed of mono-, di- or triglyceryl esters of long chain $C_{10}$–$C_{24}$ fatty acids. The mono-, di-, or triglycerides are composed predominantly of stearates, palmitates, laurates, linoleates, linolenates, oleates, and residues or mixtures thereof, having melting points greater than 50° C. are most preferred. Glyceryl tristearate is a most preferred fat. Additionally, lipophilic salts of fatty acids such as magnesium stearate and the like are also suitable.

The oil, semi-soft fat or fatty acid derivative of the invention are agents which are soluble in the molten hard fat and which accelerate physical transformation of the hard fat crystal from less stable forms to more stable forms at or near room temperature after the molten hard fat or wax has been prilled. Preferably, the oil or semi-soft fat may include mixtures or relatively pure forms of mono-, di-, or triglyceryl esters with short to medium fatty acid chain lengths, that is $C_2$ to $C_{18}$. Semi-soft fats refer to glyceryl esters having melting points at or near room temperature. Fatty acid derivatives include short and medium chain length fatty acids, alcohols, esters, ethers, salts or mixtures thereof. Glyceride oils and semi-soft fats are particularly suitable because they are physiological constituents of the body and are biocompatible and biodegradable.

The microspheres of the invention are dispersed in a pharmaceutically and pharmacologically acceptable liquid to obtain a slow release composition for parenteral administration. The vehicle may be aqueous buffered systems or oil systems. The oil system may be derived from animal or vegetable sources or be synthetic. Preferred vehicles include neutral mono-, di- or triglyceride liquid or mixtures thereof. A neutral oil is one containing no residual acid. Vehicles suitable for use in the compositions of this invention include aqueous systems such as buffered salines; organic solvents such as glycols and alcohols; and water immiscible liquids such as oils, depending upon the solubility of the active ingredient being administered.

Biologically active proteins, peptides and polypeptides suitable for administration in the compositions of the invention include growth hormones, somatomedins, growth factors, and other biologically active fragments and derivatives thereof. Preferred proteins include bovine, ovine, equine, porcine, avian, and human growth hormones; and is meant to encompass those which are of natural, synthetic, recombinant or biosynthetic origin. Additionally, metals or metal compounds associated with biologically active proteins, peptides and polypeptides, as well as acid salts, derivatives and complexes and antihydrating agents are suitable for incorporation into the composition of the invention.

Stabilizers, preservatives, surfactants, salts, buffers or mixtures thereof may optionally be included in the compositions of the invention. Preferred stabilizers include dehydroacetic acid, salicylanilide, sorbic acid, boric acid, benzoic acid, and salts thereof; sodium nitrite and sodium nitrate. If desired, the amounts of said materials suitable for use in the invention range from about 0.1% to 20% on a weight basis.

Preferred surfactants for use in compositions of the invention containing biologically active macromolecules are non-ionic in nature such as polyoxyethylene sorbitan mono-oleate (20 moles ethoxylation), and block copolymers of ethylene-oxide and propylene oxide. The amounts of surfactants suitable for use in the invention range from about 0.1% to 10.0% on a weight basis.

Uniquely, it has been found that increased blood levels of growth hormones may be obtained and maintained for extended periods of time, as can increased weight gains and increased milk production in lactating animals by injecting animals with the compositions of the invention in a suitable vehicle. Elevated blood levels of the biologically active proteins, peptides and polypeptides are generally observed and associated with beneficial and/or therapeutic effects. The effects include weight gain, increased growth rate, increased milk production in lactating animals and associated increased availability milk to nursing offspring of treated animals, improved muscle size, improved feed efficiency, decreased body fat and improved the lean meat to fat ratio. Maintaining the elevated blood levels is an indication of the slow release of the active ingredient. Properties such as increased milk production, growth rate, improved feed efficiency and increased lean meat are generally observed when elevated blood levels of the active ingredient are maintained. The invention includes the use of the compositions herein to improve milk production, increase growth rate, improve feed efficiency, increase lean meat in animals, increase and maintain levels of hormones in the blood stream of animals.

A preferred embodiment of this invention involves the incorporation of the biologically active protein, peptide or polypeptide in fat or wax microspheres and oil or semi-soft fat which may optionally also contain some or all of the excipients described above, which are then dispersed in the vehicle. The microspheres, preferably fat microspheres, may be up to 1,000 microns in diameter, with a weight average size range of 25 microns to 300 microns being preferred for parenteral administration. Microspheres containing up to about 70% of a biologically active protein, peptide or polypeptide exhibit sustained release for various periods of time depending upon the solubility of the active ingredient and the nature of the wax or fat, surfactant, buffer and vehicle employed.

The invention in its broadest sense is a slow release composition comprising a mixture of the fat or wax or mixture thereof, a biologically active protein, peptide or polypeptide drug and an oil, semi-soft fat, fatty acid derivative or mixture thereof dispersed in a pharmaceutically and pharmacologically acceptable vehicle. Microspheres and coated protein particles may be present in the slow release composition. The composition may be the protein dissolved in the fat or wax or there may be hydrophobic interaction or bonding of the active ingredient to the fat or wax. For the administration of hormone, compositions comprising on a weight basis about 1% to 70% of growth hormone, somatomedin, growth factor or biologically active fragment or derivative thereof preferably having a weight average particle size less than 20 microns; about 5% to 60% and preferably about 10% to 48% of the fat, wax or mixture thereof; about 1% to 30% and preferably 5% to 20% of the oil; optionally containing up to about 15% of the excipients such as surfactants, stabilizers, preservatives, salts or buffers or mixtures thereof with sufficient amount of a pharmaceutically and pharmacologically acceptable liquid vehicle to total 100%. The vehicle is again the aqueous buffered or oil system described above.

For the parenteral administration of growth hormones such as bovine growth hormone, microspheres comprising on a weight basis of about 5% to 40% of the solid hormone preferably having a weight average particle size of less than 20 microns, containing up to about 20% of the other excipients as described above in about 40% of 95% of fat or wax or a mixture thereof; having a weight average particle size range of 25 microns to 300 microns have demonstrated sustained release of the hormone and sustained increases in milk production in lactating dairy cows for about two weeks and are preferred. These preferred compositions have demonstrated increased milk production which is comparable to that obtained by daily injection of bovine growth hormone.

For the administration of compositions containing water soluble proteins, peptides or polypeptides such as bovine growth hormone, water immiscible liquids are preferred, with oils or liquid fats and water immiscible alcohols and glycols and mixtures thereof being more preferred. The vehicles are chosen so as to both disperse and coat the mixture of microspheres and also to provide an acceptable viscosity of the injection mixture using HLB values (Hydrophilic Lipophilic Balance) and viscosity as criteria for their selection.

On this basis, fatty acid glycerides and blends thereof which are liquid at ambient temperatures including synthetic oils; vegetable oils, such as olive, sesame seed, peanut, sunflower seed, soybean, cottonseed, corn, safflower, palm, rapeseed and coconut; animal oils such as fish oils, fish liver oils, sperm oils; or fractions derived therefrom; and mixtures thereof; having HLB values in a range of 1 to 5 and viscosities in a range of from 10 cps to 1000 cps as measured with a Brookfield viscometer RTV using a #1 spindle find utility as vehicles for compositions of the present invention.

The microspheres of the invention may be prepared by incorporating the active ingredient, having the desired particle size, and other excipients with a molten fat, wax or mixture thereof admixing the oil, semi-soft fat and/or fatty acid derivatives and then forming microspheres of the resulting mixture by a variety of techniques such as emulsifying or atomizing (or prilling) the mixture or by processing the mixture of ingredients and molten fat, wax or mixture thereof mechanically and cooling, for example utilizing a centrifugal disc. Alternatively, the mixture of active ingredients, excipients, fat, waxes and mixtures thereof and oil, may be cooled to give a solid which may then be processed by procedures such as milling, grinding and the like.

Mixtures of the invention suitable for injection are readily prepared by dispersing the protein, peptide or polypeptide, excipients, fat, wax or mixture thereof, and oil at elevated temperatures directly in the vehicle and cooling.

Microspheres of most fats and mixtures of fats and/or waxes when prepared by spray atomization from the hot melt produces particles whose crystal form based on DSC analysis is mostly unstable alpha form. Hard fats such as tristearin and tripalmitin when spray atomized retain the alpha crystal form for many months when stored at typical room temperatures. Surprisingly, mixtures of hard fats with liquid fats when melt blended and spray atomized to form prills or microspheres show accelerated transformation of alpha to beta crystal at room temperature, show markedly improved physical stability, and consequently achieve exceptional attributes for pharmaceutical parenteral compositions. Depending on the mixture, the transformation is substantially complete within several hours to several days. Appropriate compositions of hard and liquid fats are as follows: 99 to 70 parts hard fats which are mono-, di-, or triglyceryl esters with fatty acids having primarily saturated hydrocarbon chain lengths of C10 to C22, preferably from C14 to C18, and of 1 to 30 parts oil(s) which are mono-, di-, or triglyceryl esters with fatty acids having hydrocarbon chain lengths of c2 to C10.

. As a consequence of the accelerated spontaneous transformation of the crystalline structure of the microspheres made with the hard and liquid fats with or without active agents, the microspheres when suspended in the vehicle show much slower increases in viscosity when stored at typical room temperatures or at typical refrigerator temperatures. Liquid glyceride esters with fatty acids in the C2 to C12 chain length are particularly appropriate for pharmaceutical excipients because they are exceptionally biocompatible and biodegradable. Microspheres thus produced to achieve rapid transformation from the unstable alpha crystal form to the thermodynamically more stable beta crystal form also exhibit the following properties: powders show good flowability, low tack, low tendency to agglomerate during storage, increased density, and greater toughness for physical processing. Further, these improved microsphere formulations have the same utility for parenteral sustained delivery of proteins, peptides, and polypeptides and for maintenance of elevated blood levels for the purpose of improved weight gain and/or milk production increases as has been disclosed in U.S. Pat. No. 4,837,381. Finally, the marked improvement in the physical handling and stability of these microspheres makes it possible to prepare and package a ready to use commercially acceptable formulation with excellent storability characteristics. The invention is further illustrated by the following non-limiting examples.

EXAMPLES 1-7

Physical Stability of Microspheres In Neutral Oil Vehicle

These examples illustrate a range of microsphere compositions which are markedly stabilized by the inclusion into the composition of 2-15 percent of oils, semi-soft fat or mixture thereof. Physical stabilization is measured by suspending the microspheres in a neutral triglyceride oil vehicle and subjecting the suspension to a testing condition designed to mimic storage of the suspension in warm ambient environments of either 30° C. (86° F.) or 38° C. (100° F.) In the test of this example, 3 grams of microspheres are suspended into 7.5 ml of neutral triglyceride oil, and the suspension is slowly rotated (2-6 RPM) at the fixed temperature until the suspension no longer flows in the container. The gelling time is the approximate elapsed time until the suspension no longer flows. Results are given in Table 1 below. Ranges for the gelling times are given when an exact time was not observed. Time is in hours unless otherwise indicated. Each lot, source, or type of hard fat was not stabilized to the same extent; rather, gelling time was dependent on the choice of hard fat and the amount and type of oil or semi-soft fat added to the microsphere composition. However, as the results show, the addition of oil or semi-soft fat significantly increased the gelling time for each particular lot, source or type of hard fat. Age of the microspheres is also given in brackets in the table below because it is an important determinant of the gelling time since crystal transformation from less stable alpha forms to more stale beta forms is time dependent.

TABLE 1

|   | Oil or Semi-Soft Fat | Gelling Time, hours Age of Microspheres [days] | |
|---|---|---|---|
|   |   | at 30° C. | at 38° C. |
| GTS[1] |   |   |   |
| 1. a. | none | 1.5 [1] |   |
| b. | none | 6-24 [14] | 10 min [29] |
| c. | 10% Miglyol[2] 812 ® | >168 [1] | 6 [15] |
| d. | 5% GDS |   | 6-24 [21] |
| 2. a. | none | 7 min [1] |   |
| b. | 10% Miglyol 812 ® |   | 1 [1] |
| c. | 10% Miglyol 812 ® |   | 2 [80] |
| 3. a. | none | <1 [1] |   |
| b. | none | 1.3 [6] | 7 min [39] |
| c. | 2% Miglyol 812 ® | 2 [8] |   |
| d. | 5% Miglyol 812 ® | 1.3 [8] | 12 min [22] |
| e. | 10% Miglyol 812 ® | 6-24 [8] | 1 [29] |
| f. | 15% Miglyol 812 ® | 24 [1] |   |
| g. | 2% GDS | <2 [1] |   |
| h. | 5% GDS | 3 [21] | 7 min [39] |
| i. | 10% GDS | 1.3 [1] |   |
| j. | 5% Triacetin | 8-24 [1] | 1.25 [8] |
| k. | 2% GDS and 10% Miglyol 812 ® | 8-24 [1] |   |
| 4. a. | none | 1.6 [1] |   |
| b. | 10% Miglyol 812 ® | 24 [1] |   |
| 5. a. | none | 6-24 [21] |   |
| b. | 10% Miglyol 812 ® | >168 [1] |   |
| 6. a. | none | 5 min [1] |   |
| b. | 10% Miglyol 812 ® | 6-24 [1] |   |
| GDS[3] |   |   |   |
| 7. a. | none |   | 1.1 [120] |
| b. | 10% Miglyol 812 ® |   | 2 [0] |

[1]Examples 1-5 were made with different lots of GTS from Huls of America, trade name Dynasan 118. Example 6 was made with material from Pfaltz and Bauer.
[2]Miglyol 812 ® is a neutral triglyceride oil marketed by the Huls of America
[3]Source of material: Gattefosse, trade name Gelucire 64/02.

EXAMPLE 8

An unstabilized glyceryl tristearate (GTS) microsphere formulation and stabilized GTS microsphere formulation are prepared having the following compositions:

| Unstabilized microspheres | 28% bovine somatotropin |
|---|---|
|  | 2% sodium benzoate |
|  | 0.14% Pluronic F68 ®[1] |
|  | 70% glyceryl tristearate |
| Stabilized Microspheres | 28% bovine somatotropin |
|  | 2% sodium benzoate |
|  | 0.14% Pluronic F68 ® |
|  | 63% glyceryl tristearate |
|  | 7% Miglyol 812 ® |

[1]Pluronic F68 ® is a block copolymer of ethylene oxide and propylene oxide sold by BASF Corporation.

Both microsphere formulations are suspended in same amount of neutral oil vehicle and stored at 25° or 4° C. Periodically, samples of these formulations are removed from storage and allowed to warm to room temperature (22°-25° C.) before measuring the viscosity (Brookfield Viscometer T spindle C, 100 RPM). Results reported in Table 2 below demonstrate that under typical conditions of storage the stabilized formulation has markedly slower increases in viscosity over time.

TABLE 2

Viscosity Comparison of Unstabilized and Stabilized GTS Microsphere Formulations

| | Viscosity (CPS) Measured at 25° C. | | | |
|---|---|---|---|---|
| | Storage at 25° C. | | Storage at 4° C. | |
| Time | Unstabilized | Stabilized | Unstabilized | Stabilized |
| 0 | 66 | 66 | 66 | 66 |
| 1 day | 452 | — | 168 | — |
| 5 day | 2300 | — | 159 | — |
| 1 wk | 7300 | 119 | 159 | 70 |
| 2 wk | — | 195 | 159 | 71 |
| 4 wk | — | 442 | — | 79 |
| 8 wk | — | 1971 | 164 | 82 |
| 13 wk | — | 2629 | 270 | 74 |
| 26 wk | — | 2629 | 624 | 70 |
| 39 wk | — | 5280 | 741 | 71 |

EXAMPLE 9

Comparison and Analysis of Milk Production

Microspheres having the same compositions as the unstabilized and stabilized microspheres in Example 8 are prepared and tested in dairy cows to evaluate milk product efficacy. For injection, the microspheres are suspended in Miglyol 812 ®, a neutral triglyceride oil. In this example, the treatments are crossed over after two two-week injection periods. That is, group B cows receive the unstabilized formulations for the first 4 weeks with injections at the beginning of weeks 1 and 3. At the beginning of week 5, 7 and 9, these cows are injected with the stabilized formulation. Group C cows receive the stabilized formulation at the beginning of weeks 1 and 3, then the unstabilized formulation at the beginning of weeks 5, 7 and 9. Results from this experiment are given in Table 3 below. A statistical comparison of the two formulations is made by determining the mean difference in response between the average milk production for each cow when dosed with the unstabilized formulation and the average milk production when dosed with the stabilized formulation. Milk production during weeks 5 and 6 are not included in the statistical analysis, because there could be interaction between the two formulations during this period. The mean difference is $-0.9 \pm 4.7\%$, which is not statistically significant, $p > 0.05$. It is concluded that the milk production from the two formulations is very nearly the same.

TABLE 3

COMPARISON AND ANALYSIS OF MILK PRODUCTION: UNSTABILIZED VS STABILIZED MICROSPHERE SUSTAINED-RELEASE FORMULATIONS

| Group | Cow | Percent Increase in Milk Biwk → | | | | | Difference* |
|---|---|---|---|---|---|---|---|
| | | 1 | 2 | 3 | 4 | 5 | |
| | | Formulation 1 | | | Formulation 2 | | |
| B | 1 | 18.5 | 24.2 | 24.6 | 15.5 | 15.4 | 5.9 |
| | 2 | 12.4 | 15.3 | 7.3 | 9.7 | 6.3 | 5.9 |
| | 3 | 5.6 | 14.3 | 13.8 | 9.9 | 9.8 | 0.2 |
| | 4 | 6.4 | 2.7 | 12.9 | 7.3 | 12.2 | −5.2 |
| | 5 | 0.9 | 4.5 | 12.8 | 7.9 | 8.1 | −5.3 |
| | 6 | −4.5 | 8.3 | 8.1 | 8.0 | 13.9 | −9.0 |
| | 7 | 8.5 | 31.9 | 33.4 | 21.7 | 24.4 | −2.9 |
| | 8 | 4.7 | 10.9 | 4.5 | 7.9 | 9.9 | −1.1 |
| | 9 | 7.4 | 16.7 | 16.4 | 14.3 | 14.3 | −2.3 |
| | 10 | 18.5 | 19.2 | 23.5 | 21.3 | 22.3 | −3.0 |
| | | Formulation 2 | | | Formulation 1 | | |
| C | 1 | −6.9 | 5.3 | 12.3 | 3.5 | 6.2 | 5.7 |
| | 2 | 4.0 | 6.5 | −3.2 | 3.0 | 5.0 | −1.2 |
| | 3 | 3.1 | 4.6 | 8.2 | 7.1 | 8.7 | 4.0 |
| | 4 | 4.3 | 10.5 | 15.4 | 9.9 | 12.3 | 3.7 |
| | 5 | 2.9 | 15.4 | 19.5 | 16.9 | 11.7 | 5.2 |
| | 6 | 4.9 | 4.8 | 9.8 | −6.9 | −13.0 | −7.4 |
| | 7 | 2.9 | 4.9 | 7.7 | 2.5 | −3.1 | −4.2 |
| | 8 | 7.7 | 11.7 | 12.7 | 9.1 | 11.9 | 1.6 |
| | 9 | 9.9 | 14.1 | 18.1 | 6.0 | 6.3 | −5.8 |
| | 10 | 13.3 | 20.4 | 23.1 | 13.5 | 15.6 | −2.6 |
| | | | | | | Mean difference | −0.9 |
| | | | | | +/− Standard Deviation | | +/−4.7 |

*The difference is for each cow and is between the average milk production while on Formulation 1 (unstabilized) in biweeks 1 & 2 for group B or biweeks 4 & 5 for group C and the average milk production while on Formulation 2 (stabilized) in biweeks 4 & 5 for group B or biweeks 1 & 2 for group C. Due to the crossover in treatments at the beginning of biweek three, the experiment is balanced with respect to the order of dosing.
Results during biweek three are not treated statistically in order to reduce the possible carryover effect of one treatment into the next. The mean difference reflects the response difference between the two formulations.

What is claimed is:

1. A improved process for preparing a microsphere composition having the steps of melt blending a fat or wax or mixture thereof, and a biologically active protein, peptide or polypeptide to form a blend and prilling said blend to form said microsphere composition, the improvement which comprises admixing about 1% to 30% of an oil, semi-soft fat, fatty acid derivative or mixture thereof before prilling said blend.

2. The process according to claim 1 wherein the blend comprises about 30% to 95% of the fat or wax or mixture thereof and about 2% to 70% of the biologically active protein peptide or polypeptide.

3. The process according to claim 2 wherein the biologically active protein is bovine, porcine or avian growth hormone.

4. The process according to claim 3 wherein the blend comprises about 5% to 20% of a neutral triglycerol oil.

5. The process according to claim 1 which further comprises suspending the microsphere composition in a pharmaceutically and pharmacologically acceptable liquid vehicle.

6. The process according to claim 5 wherein the vehicle is an aqueous buffered system or an oil system.

7. A microsphere composition prepared in accordance with the process of claim 1.

8. A improved microsphere composition having fat or wax or mixture thereof and a biologically active protein, peptide or polypeptide, the improvement comprising about 1% to 30% of an oil, semi-soft fat, fatty acid derivative or mixture thereof.

9. The microsphere composition according to claim 8 wherein the composition comprises about 30% to 95% of the fat or wax or mixture thereof and about 2% to 70% of the biologically active protein peptide or polypeptide.

10. The microsphere composition according to claim 9 wherein the biologically active protein is bovine, porcine or avian growth hormone.

11. The microsphere composition according to claim 10 wherein the oil is a neutral triglyceride oil and the composition comprises about 5% to 20% of the oil.

12. A microsphere composition for parenteral administration comprising on a weight basis about 30% to 95% of a fat or wax or mixture thereof; about 2% to 70% of a biologically active protein, peptide or polypeptide; and about 1% to 30% of an oil, semi-soft fat, fatty acid derivative or mixture thereof.

13. The microsphere composition according to claim 12 comprising about 5% to 20% of the oil.

14. The microsphere composition according to claim 12 wherein the biologically active protein is bovine, porcine or avian growth hormone.

15. The microsphere composition according to claim 14 wherein the oil is a neutral triglycerol oil.

16. The microsphere composition according to claim 2 for parenteral administration and slow release in a pharmaceutically and pharmacologically acceptable liquid vehicle.

17. The microsphere composition according to claim 16 wherein the vehicle is an aqueous buffered system or an oil system.

18. A process for preparing a microsphere composition which comprises: melt blending on a weight basis about 30% to 95% of a fat or wax or mixture thereof, about 2% to 70% of a biologically active protein, peptide or polypeptide and about 1% to 30% of an oil to form a blend; and prilling said blend to form said composition.

19. The process according to claim 18 wherein the blend comprises 5% to 20% of the oil.

20. The process according to claim 19 wherein the oil is a neutral triglycerol oil and the biologically active protein is bovine, porcine or avian growth hormone.

* * * * *